United States Patent [19]

Thanawalla et al.

[11] 4,346,710
[45] Aug. 31, 1982

[54] ARTICLE FOR STORAGE AND TRANSPORT OF BIOGENIC FLUIDS

[75] Inventors: Chandrakant B. Thanawalla, Exton; John R. Soulen, Narberth; Harold G. Monsimer, Norristown, all of Pa.

[73] Assignee: Pennwalt Corporation, Philadelphia, Pa.

[21] Appl. No.: 148,000

[22] Filed: May 12, 1980

Related U.S. Application Data

[63] Continuation-in-part of Ser. No. 916,454, Jun. 16, 1978, abandoned.

[51] Int. Cl.$^3$ ............................................. A61J 1/00
[52] U.S. Cl. .......................... 128/272; 128/DIG. 24
[58] Field of Search .......... 260/80.5; 128/272, 214 D, 128/214 R, 348, DIG. 24

[56] References Cited

U.S. PATENT DOCUMENTS

| | | | |
|---|---|---|---|
| 2,968,649 | 1/1961 | Pailthorp et al. | 260/80.5 |
| 3,257,072 | 6/1966 | Reynolds | 128/272 |
| 3,476,506 | 11/1969 | Anderson et al. | 21/91 |
| 3,716,961 | 2/1973 | Cope et al. | 53/21 FC |

FOREIGN PATENT DOCUMENTS

2089788 of 0000 France.

Primary Examiner—Henry J. Recla
Assistant Examiner—T. J. Wallen

[57] ABSTRACT

An article for storage and transport of biogenic fluids such as blood, blood fractions, intravenous feeding solutions and liquid phase-delivered drugs is formed of an additive-free uncharged thermoplastic polymer of vinylidene fluoride copolymerized with a monomer.

3 Claims, 4 Drawing Figures

ARTICLE FOR STORAGE AND TRANSPORT OF BIOGENIC FLUIDS

CROSS-REFERENCE TO RELATED PATENT APPLICATION

This patent application is a continuation-in-part of U.S. Ser. No. 916,454, for Blood Storage Article and Methods, filed June 16, 1978 by C. B. Thanawalla and J. R. Soulen and assigned to Pennwalt Corporation, now abandoned.

BACKGROUND OF THE INVENTION

1. Field of the Invention

This invention relates to articles and methods for storage and transport of biogenic fluids such as blood, blood fractions, intravenous feeding solutions and liquid phase-delivered drugs.

2. Description of the Prior Art

Biogenic fluids include blood, blood fractions, intravenous feeding solutions and liquid phase-delivered drugs and are normally introduced to a patient intravenously or intramuscularly. All biogenic fluids must be stored and transported with extreme care, to avoid contamination and physical and chemical breakdown of the fluid.

The prior art is largely concerned with storage and transport of blood and blood fractions.

Use of polymers, having negatively charged monomer constituent elements, to store blood, to thereby minimize blood clotting, is disclosed by U.S. Pat. No. 3,633,578.

U.S. Pat. No. 3,723,754, French patent publication 2,089,788 and Japanese application Ser. No. 45/75116, the convention application from which the U.S. and French applications derive their priority dates, disclose a device for blood storage and for dynamic flow of blood therethrough, fabricated as an electret having a stable heterocharge and constructed so the negative charge bearing surface of the electret contacts the blood, to reduce clotting as the blood touches the device. These references teach that the device may be constructed of polyvinylidene fluoride.

Two problems plague flexible plastics known for use in storing and handling biogenic fluids such as blood. First, flexible plastics used to store biogenic fluids contain leachables which enter the fluid from the container (made of the flexible plastic) in which the fluid is stored. It is not known whether the leachables adversely affect the fluid per se, however, it is postulated that they may have extremely undesirable effects on the patient into whom the fluid is introduced. Second, in the case of blood, red blood cells deteriorate upon contact with many materials in which biogenic fluids, including blood, are currently stored; this deterioration phenomenon is "red cell hemolysis." This manifests itself as cell rupture and results in release of hemoglobin from the red cells into the blood plasma, rendering the blood incapable of carrying oxygen.

The relationship, if any, between these two problems is unknown.

Concerning leachables, plasticizers such as Di-2-ethylhexyl phthalate (DEHP) form up to 40% of the dry weight of flexible plastic currently used to store and transport biogenic fluids. These plasticizers leach from flexible plastic into any blood or blood components stored in the plastic. This has been reported in the *New England Journal of Medicine*, Volume 292, No. 8, "Identification and Measurement of Plasticizer in Neonatal Tissues After Umbilical Catheters and Blood Products," Feb. 20, 1975, and in the *Journal of Transfusion*, Volume 16, No. 4, "Fate in Humans of the Plasticizers Di-2-Ethylhexyl Phthalate Arising from Transfusion of Platelets Stored in Vinyl Plastic Bags," July/August 1976.

Two adverse effects of these plasticizers have been identified: When blood containing DEHP is transfused into a pregnant rat, the DEHP migrates from the mother into the fetus. This produces a teratogenic effect on the unborn fetus; DEHP may have the same effect on humans. See *Journal of Pharmaceutical Sciences*, Volume 64, No. 8, "Maternal-Fetal Transfer of 14C-Di-2-Ethylhexyl Phthalate and 14-C-Diethyl Phthalate in Rats," August 1975. Additionally, DEHP, when administered via injection, damages rats' lungs. From this researchers have postulated that DEHP might be the cause of "shock lung," a frequent cause of death among humans receiving massive blood transfusions during surgery. See *Chemical & Engineering News*, June 9, 1975, page 5.

Red cell hemolysis during blood storage is recognized in U.S. Pat. No. 3,257,072, which discloses apparatus and a method for storing blood. The '072 method utilizes a container having two storage volumes formed of fluorinated ethylene propylene or of polytetrafluoroethylene. These materials yield only a translucent storage container; they generally do not require plasticizers to be flexible. Fluorocarbon polymers, such as those disclosed in the '072 patent, are known to exhibit superior resistance to chemical and biological attack. See the *Handbook of Biomedical Plastics*, Pasedena Technology Press, copyright 1971.

A consideration in choosing materials for storage and transport of biogenic fluids is the sterilizability of a candidate material.

The preferred commercial method of sterilizing articles made of thin plastic film used for storage and transport of biogenic fluid utilizes ethylene oxide. Sterilization is performed at room temperature and at approximately atmospheric pressure. The fluid storage and transport articles made of the plastic film are sealed and maintained in an ethylene oxide environment for a time which is a function of the film material. The articles are then removed from the ethylene oxide environment and taken to a storage area where they are maintained under clean conditions until free of ethylene oxide and by-products; this takes from two (2) to three (3) weeks. Lengthy storage is necessary to allow the ethylene oxide to escape from the articles interior through the film and to outgas from the film itself.

Theory of gas transport through plastic films is not well enough developed to allow accurate prediction of rate of transport of a particular gas, such as ethylene oxide, through film. A leading reference on gas transport through films is *The Science and Technology of Polymeric Films* published by Wiley-Interscience, Inc., copyright 1971. This reference discloses that (1) polymer films act as barriers to gas if the films are free of macroscopic defects such as pinholes and cracks and (2) gas transport through polymer films is a function of the morphology and molecular topology of the polymer and of the chemical compositions of the polymer and the gas of interest. This reference hypothesizes that two distinct mechanisms contribute to such gas transport. The two hypothesized mechanisms are (1) gas migration via microscopic and smaller pores through the polymer film and (2) gas dissolution into the polymer film at the film surface followed by gas diffusion through the film due to gas concentration gradient therewithin.

Hypotheses such as the foregoing represent the leading edge of gas transport theory; the theory is not sufficiently advanced to permit qualitative or quantitative selection of polymers providing maximum transport rate of a given gas. Consequently, there is no adequate theory to permit qualitative or quantitative selection of plastics for biogenic fluid storage based on time required for gas sterilization of an article made of a particular plastic.

Patents which disclose various polymers and methods of making same, which may be of background interest, are U.S. Pat. Nos. 2,968,649; 3,193,539; 3,790,540 and 3,857,827. None of these disclose apparatus or methods for storage or transport of biogenic fluids.

SUMMARY OF THE INVENTION

This invention provides a transparent article for storing and transporting biogenic fluid, formed of additive-free uncharged transparent thermoplastic film of a polymer of vinylidene fluoride copolymerized with at least one monomer selected from the group consisting of tetrafluoroethylene and hexafluoropropene, where the vinylidene fluoride constitutes at least sixty-two percent by weight of the copolymer composition. The transparent character of the article allows visual inspection of the contents without opening the article and rendering the contents unsterile. The article maintains its flexible character even at very low temperatures at which biogenic fluid may be stored and processed; thus the article can be handled even at very low fluid storage and processing temperatures without the article breaking. Surprisingly, the thermoplastic from which the article is made exhibits unexpectedly high permeability to ethylene oxide, the commercially preferred gas for sterilization of biogenic fluid storage and transport articles, facilitating rapid sterilization of the articles. Blood stored and transported via the article exhibits minimal red cell hemolysis and is not subject to leaching contamination.

DESCRIPTION OF THE PREFERRED EMBODIMENTS

This invention provides a transparent article for storing and transporting biogenic fluid, formed of additive-free uncharged transparent thermoplastic of a polymer of vinylidene fluoride. It is not necessary to convert the vinylidene fluoride copolymer into an electret before the article is fabricated. The transparent character of the article fabricated of the vinylidene fluoride copolymer allows visual inspection of biogenic fluid therewithin without opening the article and thereby risking contamination of the contents. The vinylidene fluoride is copolymerized with one or more monomers; the monomers are selected from the group consisting of tetrafluoroethylene and hexafluoropropene. The article of the invention is formed from a film of the resulting copolymer.

"Biogenic fluid" as used herein includes blood, blood fractions, intravenous feeding solutions, liquid phase drugs, solid phase drugs or other solid materials suspended in liquids for parenteral administration and other biologically active therapeutic substances in liquid phase.

"Vinylidene fluoride copolymer" as used herein means polymers of vinylidene fluoride copolymerized with monomers selected from the group consisting of tetrafluoroethylene and hexafluoropropene.

The adjectives "charged" and "poled," and variants thereof, as used herein denote films which have had an electrical charge intentionally imposed thereon by exposure to an electrical field. The adjectives "uncharged" and "unpoled," and variants thereof, denote films which have not had an electrical charge intentionally imposed thereon.

The term "additive free," and variants thereof, denotes polymers which are devoid of plasticizers and which have had nothing added thereto after the polymer has been synthesized.

When the invention is used to store and transport blood, red cell hemolysis of the blood is reduced from that experienced when blood is stored and transported in an article of polyvinyl chloride, the material currently most widely used commercially. When the article is fabricated from films of the preferred vinylidene fluoride copolymers, a sufficiently flexible article results without the addition of any plasticizers to the copolymer film; this eliminates the danger of any plasticizer leaching into the blood or any other biogenic fluid stored or transported in the article. The preferred films have a dynamic modulus of between $0.03 \times 10^{10}$ dynes/cm$^2$ and $5.0 \times 10^{10}$ dynes/cm$^2$ over a temperature range of from $-80°$ C. to $+25°$ C.

The manner and process of making and using the invention are illuminated by the following examples.

EXAMPLE 1

A polymer of twenty-seven percent (27%) by weight tetrafluoroethylene and seventy-three percent (73%) by weight vinylidene fluoride was prepared using the procedure described in U.S. patent 3,193,539, incorporated herein by reference. The polymer was then extruded into a flexible film. Using a Rheovibron Dynamic Viscoelastometer, Model DDV-II, the dynamic modulus of the extruded film was measured at eleven (11) cps over a temperature range of from $-80°$ C. to $100°$ C. and was found to be $0.73 \times 10^{10}$ dynes/cm$^2$ at $25°$ C. and $3.6 \times 10^{10}$ dynes/cm$^2$ at $-80°$ C. Optical transmission over the visible spectrum was ninety percent (90%) through a three mil (0.003 inch) thickness of the film. Biological tests required for plastic containers, recited in U.S. Pharmacopoeia, Volume XIX, showed that the material was a Class VI plastic. Following procedures specified in U.S. Pharmacopoeia, Volume XIX, the film was found to be pyrogen-free. Several bags were formed from portions of the film by heat sealing the edges of two congruent portions of the film.

Human blood was processed by conventional centrifugation to yield separate components of packed red cells and plasma. A portion of the packed red cells was then stored for several days at low temperature in some of the bags which had been sterilized with ethylene oxide gas in the conventional manner; a remaining portion of the packed red cells was stored for several days at low temperature in some of the bags which had been radiation sterilized. The two portions of red cells were then thawed, washed and reconstituted in the conventional manner. When the reconstituted red cells stored in the ethylene oxide gas-sterilized film bags were subjected to the American Red Cross red cell hemolysis test they were found to have 104 milligrams of free hemoglobin (released from ruptured red cells) per 100 cc of red cells as reconstituted. When the reconstituted red cells stored in the radiation-sterilized film bags were subjected to the American Red Cross red cell hemolysis test they were found to have 102 milligrams of free hemoglobin per 100 cc of red cells as reconstituted.

EXAMPLE 2

A polymer of twenty-four percent (24%) by weight tetrafluoroethylene, fourteen percent (14%) by weight hexafluoropropene and sixty-two percent (62) by weight vinylidene fluoride was prepared using the procedure described in U.S. Pat. No. 3,857,827, incorporated herein by reference. The polymer was then extruded into a flexible film. Using a Rheovibron Dynamic Viscoelastometer, Model DDV-II, the dynamic modulus of the extruded film was measured at eleven (11) cps over a temperature range of from $-80°$ C. to $100°$ C. and was found to be $0.095 \times 10$ dynes/cm$^2$ at $25°$ C. and $3.3 \times 10^{10}$ dynes/cm$^2$ at $-80°$ C. Optical transmission over the visible spectrum was ninety-two percent (92%) through a five mil (0.005 inch) thickness of the film. Biological tests required for plastic containers, recited in U.S. Pharmacopoeia Volume XIX, showed that the material was a Class VI plastic. Following procedures specified in U.S. Pharmacopoeia, Volume XIX, the film was found to be pyrogen-free. Several bags were formed from portions of the film by heat sealing the edges of two congruent portions of the film.

Human blood was processed by conventional centrifugation to yield separate components of packed red cells and plasma. A portion of the packed red cells was then stored for several days at low temperature in some of the bags which had been sterilized with ethylene oxide gas in the conventional manner; a remaining portion of the packed red cells was stored for several days at low temperature in some of the bags which had been radiation sterilized. The two portions of red cells were then thawed, washed and reconstituted in the conventional manner. When the reconstituted red cells stored in the ethylene oxide gas-sterilized film bags were subjected to the American Red Cross red cell hemolysis test they were found to have 91 milligrams of free hemoglobin (released from ruptured red cells) per 100 cc of red cells as reconstituted. When the reconstituted red cells stored in the radiation-sterilized film bags were subjected to the American Red Cross red cell hemolysis test they were found to have 101 milligrams of free hemoglobin per 100 cc of red cells as reconstituted.

Bags were formed from three samples of commercially available polyvinyl chloride (PVC) film by heat sealing the edges of two congruent portions of the films. Conventionally separated, packed red cells from human blood were stored in the bags fabricated from the PVC. Red cell separation and storage was performed in the same manner and under the same conditions as recited in Examples 1 and 2 above. When the red cells were removed from the bags fabricated from the three samples of polyvinyl chloride and subjected to the American Red Cross red cell hemolysis test, the bags from the three samples had, respectively, 142, 214 and 152 milligrams of free hemoglobin (released from ruptured red cells) per 100 cc of red cells as reconstituted.

The following table presents a comparison of hemolysis of red cells stored in bags as recited in Examples 1 and 2 with hemolysis of red cells stored in bags fabricated from the commercially available polyvinyl chloride:

TABLE 1

| Sample | Hemolysis mg Hemoglobin/100 cc of red cells as reconstituted |
|---|---|
| Example 1, ethylene oxide gas sterilized | 104 |
| Example 1, radiation sterilized | 102 |
| Example 2, ethylene oxide gas sterilized | 91 |
| Example 2, radiation sterilized | 101 |
| Commercially available PVC | 142 |
| Commercially available PVC | 214 |
| Commercially available PVC | 152 |

When the film bag of Example 1 was used, red cell hemolysis was reduced, on the average, by thirty-four percent (34%) over that experienced, on the average, using a film bag fabricated of commerically available polyvinyl chloride. When the film bag of Example 2 was used, red cell hemolysis was reduced, on the average, by forty-three percent (43%) over that experienced, on the average, using a film bag fabricated of commercially available polyvinyl chloride.

EXAMPLE 3

Using the process of U.S. Pat. No. 3,193,539, a polymer of seventy percent (70%) by weight vinylidene fluoride and thirty percent (30%) by weight tetrafluoroethylene was prepared and extruded into a film. The film was divided into two portions. The first portion was formed into two bags by dividing the film portion in half, folding the resulting halves of film over themselves and applying heat to the film margins. The second portion was given an electrical charge, i.e. "poled," by placing the film between two electrodes; this second poled portion was then formed into two bags by dividing the film portion in half, folding the resulting charged halves of film over themselves and applying heat to heat seal the film margins. The four bags were then delivered to the American Red Cross for testing.

Aliquot portions of red blood cells were separated from a common unit of human blood, glycerolized and thereafter stored in the four bags for eight days at a temperature of $-80°$ C. The aliquot portions were then thawed, washed, reconstituted and subjected to the Red Cross red cell hemolysis test. The test results follow:

TABLE 2

| Sample | Percent Red Cell Hemolysis |
|---|---|
| Uncharged Film | 1.0 |
| Uncharged Film | 0.6 |
| Charged Film | 0.7 |
| Charged Film | 0.6 |

Red cell hemolysis exhibited by samples stored in the charged film and in the uncharged film was, within the limits of experimental error, the same.

EXAMPLE 4

Using the process of U.S. Pat. No. 3,857,827, a polymer of sixty-two percent (62%) by weight vinylidene fluoride, twenty-four percent (24%) by weight tetrafluoroethylene and fourteen percent (14%) by weight hexafluoropropene was prepared and extruded into a film. The film was divided into two portions. The first portion was formed into two bags by dividing the film portion in half, folding the resulting halves of film over themselves and applying heat to heat seal the film margins. The second portion was given an electrical charge, i.e. "poled," by placing the film between two electrodes; the second portion was then formed into two bags by dividing the film portions in half, folding the resulting charged halves of film over themselves and applying heat to heat seal the film margins. The four bags were then delivered to the American Red Cross for testing.

Aliquot portions of red blood cells were separated from a common unit of human blood, glycerolized and thereafter stored in the four bags for eight days at a temperature of $-80°$ C. The aliquot portions were then thawed, washed, reconstituted and subjected to the Red Cross red cell hemolysis test. The test results follow:

TABLE 3

| Sample | Percent Red Cell Hemolysis |
|---|---|
| Uncharged film | 0.7 |
| Uncharged film | 0.6 |
| Charged film | 0.7 |
| Charged film | 0.6 |

The red cell hemolysis exhibited by samples stored in the charged film and in the uncharged film was, within the limits of experimental error, the same.

A polymer of fifteen percent (15%) by weight hexafluoropropene and eighty-five percent (85%) by weight vinylidene fluoride has been prepared using the procedure of U.S. Pat. No. 3,193,539 and extruded into a flexible film. Using a Rheovibron Dynamic Viscoelastometer, Model DDV-II, the dynamic modulus of the film, measured at eleven (11) cps over a temperature range of from $-80°$ C. to $100°$, is $0.37 \times 10^{10}$ dynes/cm$^2$ at $25°$ C. and is $2.5 \times 10^{10}$ dynes/cm$^2$ at $-80°$ C. Optical transmission over the visible spectrum is ninety percent (90%) through a three mil (0.003 inch) thickness of the film.

Laboratory work has revealed that the vinylidene fluoride copolymers of Examples 1-4 above, containing at least sixty-two percent (62%) vinylidene fluoride copolymerized with tetrafluoroethylene and hexafluoropropene, exhibit permeability to ethylene oxide which is several orders of magnitude greater than that of homopolymers of tetrafluoroethylene, fluorinated ethylene propylene or vinylidene fluoride. High permeability to ethylene oxide makes these polymer films containing at least sixty-two percent (62%) vinylidene fluoride as recited in Examples 1-4 above preferred for fabrication of articles which would subsequently be sterilized using ethylene oxide gas. Such articles include, but are not limited to, articles for storage and transport of biogenic fluid. The high permeability of these films to ethylene oxide results in rapid transport of ethylene oxide through the film to the interior of the film article with sufficiently high concentration of ethylene oxide building up in a short time, even in sealed-off nooks and crannies, to affect sterilization of the film article. High permeability to ethylene oxide also results in rapid outgassing of the ethylene oxide for the article after sterilization has been effected. Rapid completion of the sterilization process will result in considerable savings when the article is commercialized.

EXAMPLE 5

One milliliter of liquid ethylene oxide was placed in each of two paired aluminum cups (obtainable as "vapormeters" from Thwing-Albert Instrument Company, Philadelphia, Pa.). The top of one cup was loosely covered with a film of 5.0 mil (0.005 inch) thick fluorinated ethylene propylene while the top of the second cup was similarly loosely covered with a film of 3.8 mil (0.0038 inch) thick vinylidene fluoride copolymer consisting of twenty-seven percent (27%) by weight tetrafluoroethylene and seventy-three percent (73%) by weight vinylidene fluoride. The open mouth at the top of each such cup is 2.5 inches (64 millimeters) in diameter, providing an opening of 32 square centimeters. After most of the liquid ethylene oxide had evaporated and hence displaced the air from the cups, the films were tightly sealed over the cups with retaining rings. The paired cups were then weighed simultaneously, at selected time intervals, to determine the amount of ethylene oxide lost through the films. Table 4 presents the measured cumulative weight loss of ethylene oxide from the two cups:

TABLE 4

| | Ethylene Oxide Lost | | | |
|---|---|---|---|---|
| | Fluorinated Ethylene Propylene 5.0 mil | | 27% Tetrafluoroethylene 73% Vinylidene Fluoride 3.8 mil | |
| Time (minutes) | Grams | % | Grams | % |
| 30 | +0.0010 | +0.9 | −0.0050 | −2.6 |
| 60 | +0.0020 | +1.7 | −0.0259 | −13.4 |
| 105 | +0.0024 | +2.0 | −0.0422 | −21.8 |
| 180 | +0.0029 | +2.5 | −0.0627 | −32.4 |
| 240 | +0.0025 | +2.2 | −0.0722 | −37.2 |

The film of twenty-seven percent tetrafluoroethylene and seventy-three percent vinylidene fluoride deformed deeply into the cup while no deformation of the fluorinated ethylene propylene film was evident. Deformation of the tetrafluoroethylene-vinylidene fluoride film corroborates the measured test data, indicating that a substantial amount of ethylene oxide had left the cup by diffusing through the film. The minus signs in the table indicate a measured weight loss while the plus signs indicate a measured weight gain. The weight gain exhibited by the fluorinated ethylene propylene covered cup is probably due to diffusion of air through the film into the cup. Whatever the cause of the weight gain, it should be noted that the measured weight gain for the fluorinated ethylene propylene covered cup is much, much smaller than the measured weight loss for the tetrafluoroethylene-vinylidene fluoride covered cup, indicating that the rate of ethylene oxide transport through the tetrafluoroethylene-vinylidene fluoride film is much, much greater than the rate of ethylene oxide transport through the fluorinated ethylene propylene film.

Figure 1:
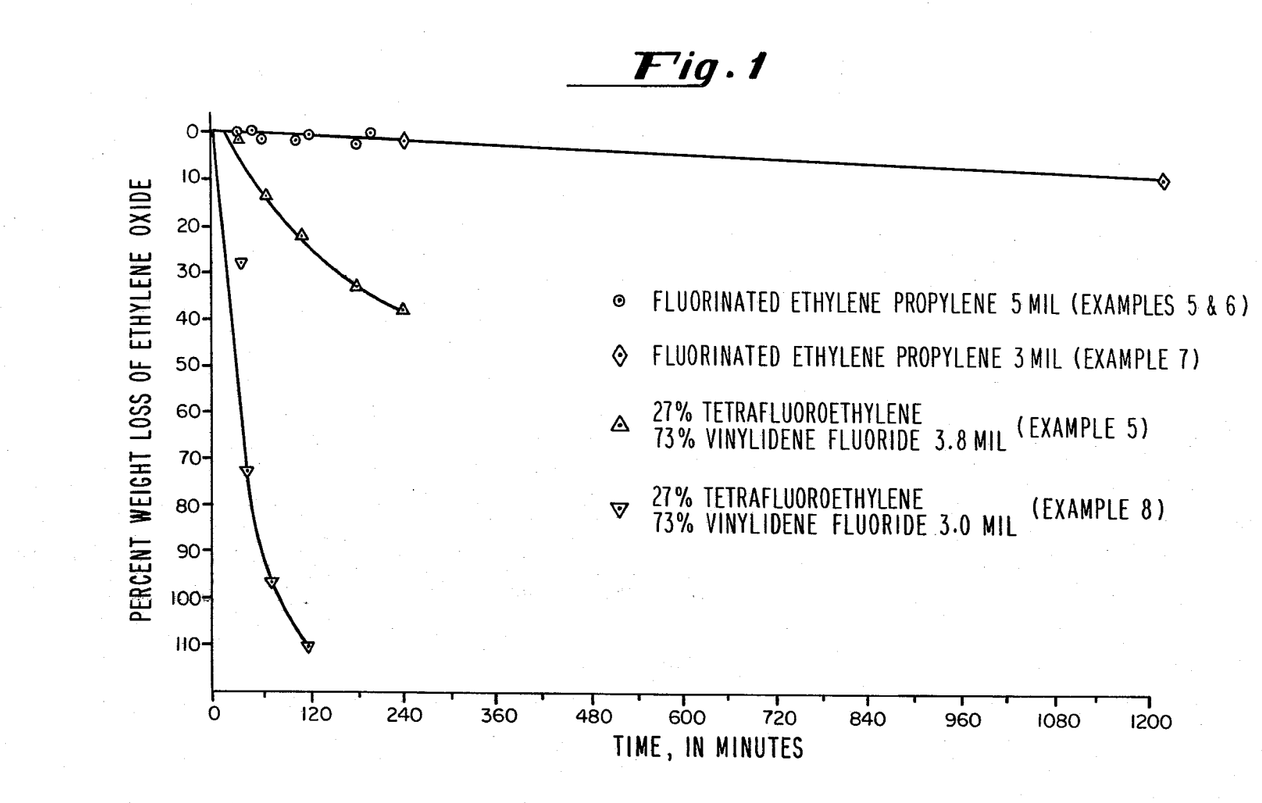
FIGS. 1, 2, 3 and 4 qualitatively show transport of ethylene oxide through various films, including films from which the article of the invention is fabricated, as a function of time.

The 3.8 mil embodiment of the invention shown in FIG. 1 and Table 4 passed 0.0095 grams of gaseous ethylene oxide through 32 sq. cm. of film in the last 60 minute period (between the 180th minute and the 240th minute) of the experiment, or $1.6 \times 10^{-4}$ grams/min/sq. cm.

EXAMPLE 6

Using the procedure described in Example 5, permeability to ethylene oxide of a 5.0 mil (0.005 inch) thick film of fluorinated ethylene propylene was compared to that of a 3.0 mil (0.003 inch) thick film consisting of twenty-seven percent (27%) by weight tetrafluoroethylene and seventy-three percent (73%) by weight vinylidene fluoride. Table 5 presents the measured cumulative weight loss of ethylene oxide from the two cups, one covered with each film:

TABLE 5

| | Ethylene Oxide Lost | | | |
|---|---|---|---|---|
| | Fluorinated Ethylene Propylene 5.0 mil | | 27% Tetrafluoroethylene 73% Vinylidene Fluoride 3.0 mil | |
| Time (minutes) | Grams | % | Grams | % |
| 30 | −0.0003 | −0.3 | −0.0342 | −26.3 |
| 45 | | | −0.0960 | −73.8 |
| 60 | −0.0003 | −0.3 | | |
| 75 | | | −0.1267 | −97.4 |
| 120 | −0.0003 | −0.3 | −0.1505 | −115.7 |
| 195 | −0.0003 | −0.3 | film imploded | |

The minus signs in the table indicate a measured weight loss. The film of twenty-seven percent tetrafluoroethylene and seventy-three percent vinylidene fluoride deformed deeply into the cup and, after three hours and fifteen minutes, imploded. No deformation of the fluorinated ethylene propylene film was evident. Deformation and implosion of the tetrafluoroethylene-vinylidene fluoride film corroborates the measured data, indicating that at least a substantial amount, and perhaps all, of the ethylene oxide had exited the cup by diffusing through the film.

Note that the data at one hundred twenty minutes shows that about one hundred fifteen percent of the initial weight of ethylene oxide in the tetrafluoroethylene-vinylidene fluoride covered cup had been lost therefrom through the film, i.e. more ethylene oxide had been lost than was originally in the cup. This apparent anomaly is easily explained: When the ethylene oxide has exited the cup by diffusing through the film, a partial vacuum exists in the cup as evidenced by the downward deformation of the tetrafluoroethylene-vinylidene fluoride film into the cup. Since fewer molecules are now in the cup as compared to when the cup is filled with air, the measured weight of the cup in the partial vacuum condition is less than that measured when the cup is open and filled with air. This decrease in measured cup weight appears in the data an additional weight of ethylene oxide lost.

EXAMPLE 7

Using the procedure described in Example 5, permeability of a 3.0 mil (0.003 inch) thick film of fluorinated ethylene propylene to ethylene oxide was evaluated. No paired sample of a vinylidene fluoride polymer film was used. Table 6 presents the measured cumulative weight loss of ethylene oxide for the cup:

TABLE 6

| | Ethylene Oxide Lost | |
|---|---|---|
| | Fluorinated Ethylene Propylene 3.0 mil | |
| Time (minutes) | Grams | % |
| 240 | 0.0034 | −3.2 |
| 1440 | 0.0098 | −9.2 |

TABLE 6-continued

| | Ethylene Oxide Lost | |
|---|---|---|
| | Fluorinated Ethylene Propylene 3.0 mil | |
| Time (minutes) | Grams | % |
| 7200 | 0.0120 | −11.3 |

The minus signs in the table indicate a measured weight loss. No deformation of the fluorinated ethylene propylene film was evident.

The 3.0 mil thick fluorinated ethylene propylene film of Table 6 and FIG. 1 passed 0.0064 grams of gaseous ethylene oxide during the 1200 minute period between the 240th minute and the 1440th minute of the test, or $1.7 \times 10^{-7}$ grams/minute/sq. cm.

EXAMPLE 8

Using the procedure described in Example 5, permeability to ethylene oxide of a 3.0 mil (0.003 inch) thick film of polytetrafluoroethylene was compared to that of a 3.0 mil (0.003 inch) thick film consisting of twenty-four percent (24%) by weight tetrafluoroethylene, fourteen percent (14%) by weight hexafluoropropene and sixty-two percent (62%) by weight vinylidene fluoride. Table 7 presents the measured cumulative weight loss of ethylene oxide from the two cups, one covered with each film:

TABLE 7

| | Ethylene Oxide Lost | | | |
|---|---|---|---|---|
| | Polytetrafluoroethylene 3.0 mil | | 24% Tetrafluoroethylene 14% Hexafluoropropene 62% Vinylidene Fluoride 3.0 mil | |
| Time (minutes) | Grams | % | Grams | % |
| 10 | | | −0.0280 | −20.6 |
| 15 | −0.0015 | — | −0.0965 | −71.0 |
| 45 | | | deformation | −87.0 |
| 105 | −0.0015 | — | −0.1183 | −108.0 |
| 240 | −0.0016 | — | −0.1359 | −114.0 |

The minus signs in the table indicate a measured weight loss. The film of tetrafluoroethylene, hexafluoropropene and vinylidene fluoride stretched downward into the cup and permanently deformed. No deformation of the polytetrafluoroethylene film was evident. The data at one hundred five and two hundred forty minutes, indicating weight loss of ethylene oxide greater than the weight of ethylene oxide in the cup initially, are indicative of the phenomenon noted above with respect to Example 6.

Figure 2:
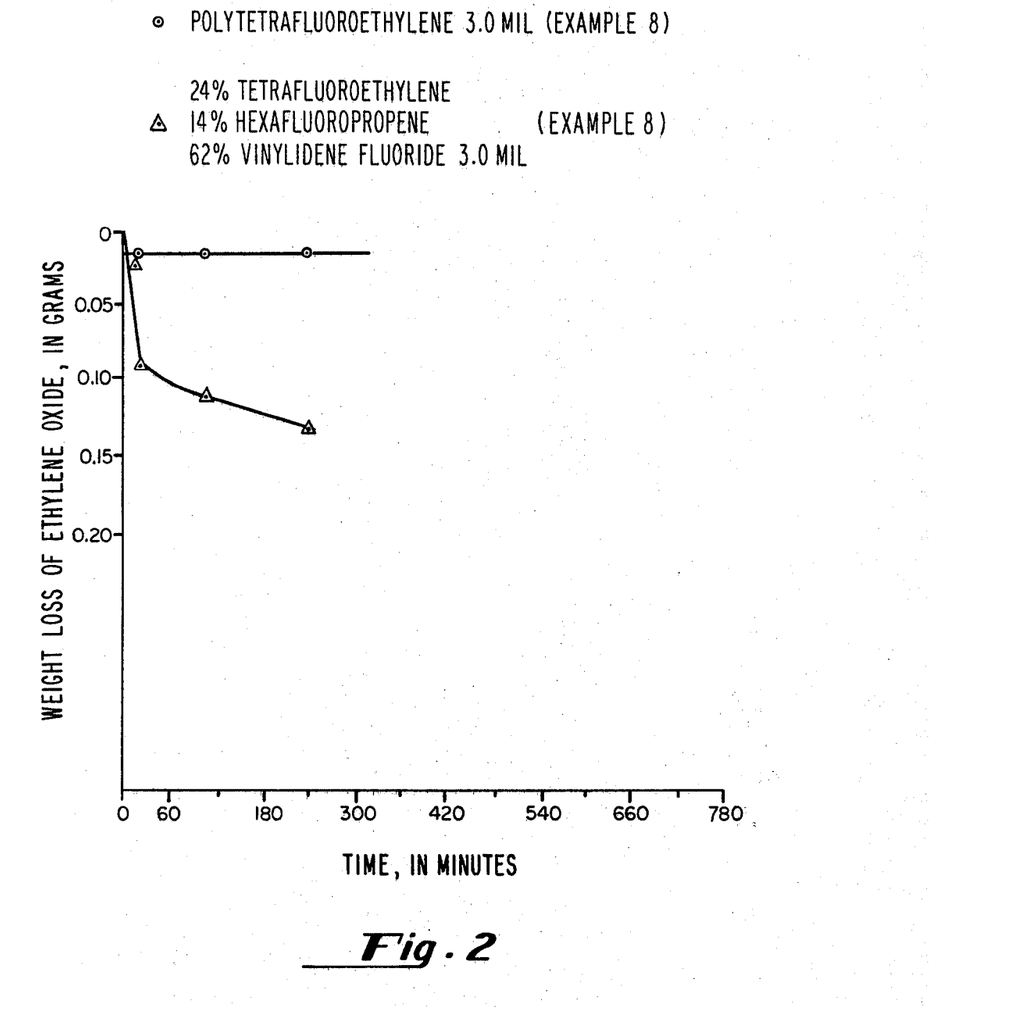

The 3.0 mil embodiment of the invention shown in FIG. 2 and Table 7 passed 0.0176 grams of gaseous ethylene oxide through 32 sq. cm. of film in the 135 minute period between the 105th minute and the 240th minute of the test, or $4.1 \times 10^{-6}$ gram/minute/sq. cm.

EXAMPLE 9

Using the procedure described in Example 5, permeability to ethylene oxide of a 5.5 mil (0.0055 inch) thick film of polyvinylidene fluoride was compared to that of a 3.5 mil (0.0035 inch) thick film consisting of twenty-seven percent (27%) by weight tetrafluoroethylene and seventy-three percent (73%) by weight vinylidene fluoride. Table 8 presents the measured cumulative weight loss of ethylene oxide from the two cups, one covered with each film:

TABLE 8

TABLE 8

| | Ethylene Oxide Lost | | | |
|---|---|---|---|---|
| | Polyvinylidene Fluoride 5.5 mil | | 27% Tetrafluoroethylene 73% Vinylidene Fluoride 3.5 mil | |
| Time (minutes) | Grams | % | Grams | % |
| 20 | −0.0015 | −3.3 | | |
| 30 | | | +0.0031 | +4.8 |
| 60 | −0.0015 | −3.3 | +0.0018 | +2.7 |
| 120 | −0.0013 | −2.9 | −0.0081 | −12.4 |
| 190 | | | −0.0222 | −33.9 |
| 240 | +0.0004 | +0.9 | | |
| 330 | +0.0015 | +3.3 | | |
| 390 | | | −0.0287 | −51.6 |
| 1440 | +0.0001 | 0.0 | −0.0692 | −105.6 |

The minus signs in the table indicate a measured weight loss. The plus signs indicate measured weight gain, which is believed to be due to air diffusion through the films into the cups, as explained above with respect to Example 5. The data at one thousand four hundred forty minutes, indicating weight loss of ethylene oxide greater than the weight of ethylene oxide in the cup initially, is indicative of the phenomenon noted above with respect to Example 6.

Figure 3:
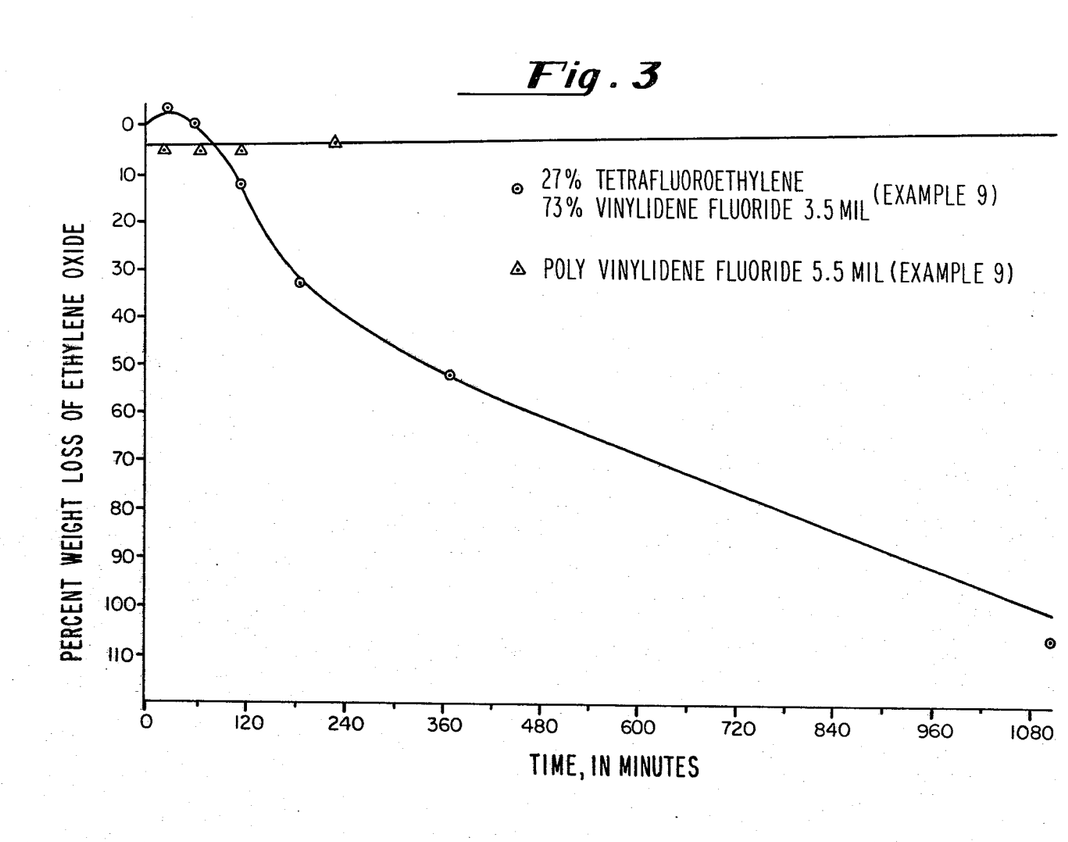

The 3.5 mil thick embodiment of the invention shown in FIG. 3 and Table 8 passed 0.0405 grams of gaseous ethylene oxide through 32 sq. cm. of film in the 1050 minute period between the 390th minute and the 1440th minute of the experiment, or $1.2 \times 10^{-6}$ grams/minute/sq. cm.

EXAMPLE 10

Using the procedure described in Example 5, permeability to ethylene oxide of a 4.0 mil (0.004 inch) thick film consisting of eight percent (8%) by weight tetrafluoroethylene and ninety-two percent (92%) by weight vinylidene fluoride was compared to that of a 3.5 mil (0.0035 inch) thick film consisting of twenty-seven percent (27%) by weight tetrafluoroethylene and seventy-three percent (73%) by weight vinylidene fluoride. Table 9 presents the measured cumulative weight loss of ethylene oxide from the two cups, one covered with each film:

TABLE 9

| | Ethylene Oxide Lost | | | |
|---|---|---|---|---|
| | 8% Tetrafluoroethylene 92% Vinylidene Fluoride 4 mil | | 27% Tetrafluoroethylene 73% Vinylidene Fluoride 3.5 mil | |
| Time (minutes) | Grams | % | Grams | % |
| 10 | +0.0025 | +1.5 | | |
| 15 | | | −0.560 | −33.1 |
| 40 | | | −0.1226 | −72.5 |
| 45 | −0.0622 | −36.3 | | |
| 65 | −0.1043 | −60.8 | | |
| 70 | | | −0.1560 | −92.2 |
| 100 | −0.1287 | −75.0 | −0.1643 | −97.2 |
| 155 | −0.1591 | −92.8 | imploded | |
| 215 | −0.1762 | −102.0 | | |

Figure 4:
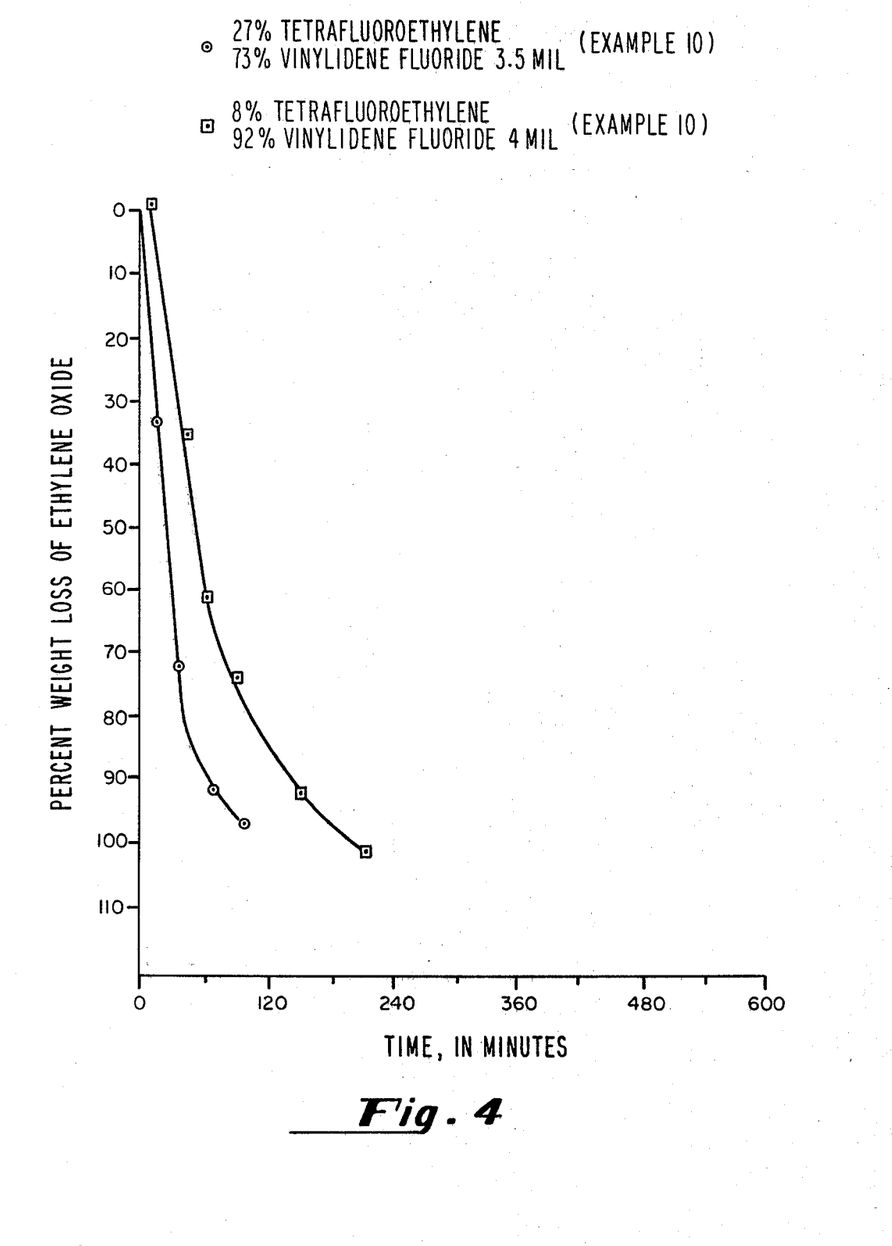

The 4 mil thick film of FIG. 4 and Table 9 passed 0.0171 grams of gaseous ethylene oxide through 32 sq. cm. of film during the 60 minute period between the 155th minute and the 215th minute of the test, or $2.9 \times 10^{-6}$ gram/minute/sq. cm.

The minus signs in the table indicate a measured weight loss. Both films deformed deeply into their respective cups, with the film consisting of twenty-seven percent tetrafluoroethylene and seventy-three percent vinylidene fluoride imploding into the cup after one hundred fifty-five minutes. The plus signs indicate measured weight gain, which is believed to be due to air diffusion through the films into the cups, as explained above with respect to Example 5. The data at two hundred fifteen minutes, indicating weight loss of ethylene oxide greater than the weight of ethylene oxide in the cup initially, is indicative of the phenomenon noted above with respect to Example 6.

The data from Examples 5, 6 and 7 are plotted in FIG. 1, the data from Example 8 in FIG. 2, the data from Example 9 in FIG. 3 and the data from Example 10 in FIG. 4.

From the data presented in Tables 4-9 and plotted in FIGS. 1-4, the dramatically greater rates of ethylene oxide transport through films consisting of at least sixty-two percent (62%) by weight vinylidene fluoride copolymerized with at least one monomer selected from the group consisting of tetrafluoroethylene and hexafluoropropene, as compared with the rate of ethylene oxide transport through films of fluorinated ethylene propylene, tetrafluoroethylene or vinylidene fluoride homopolymers, is apparent. FIGS. 1 through 4 reveal that the homopolymers are substantially impermeable to ethylene oxide, as demonstrated by the generally horizontal lines in FIGS. 1, 2 and 3, while the films of the copolymers of vinylidene fluoride permit rapid diffusion of ethylene oxide therethrough. In every case rate of ethylene oxide transport through the films of the copolymers of vinylidene fluoride is at least an order of magnitude greather than through films of the homopolymers. Thus the addition of at least sixty-two percent (62%) by weight of vinylidene fluoride to the films produces at least an order of magnitude increase in the permeability of the film to ethylene oxide.

This improved permeability to ethylene oxide of copolymer film containing at least sixty-two percent (62%) vinylidene fluoride over the homopolymer films means that the biogenic fluid storage and transport articles of the invention, when fabricated of a film containing at least sixty-two percent (62%) by weight vinylidene fluoride copolymerized with at least one monomer selected from the group consisting of tetrafluoroethylene and hexafluoropropene, will be ethylene oxide sterilizable in an order of magnitude less time than required for articles made of the above-recited homopolymers. This should result in considerable cost and energy savings.

Although Examples 1 through 4 speak to storage of blood in bags formed from films of polymers of at least sixty-two percent (62%) by weight vinylidene fluoride copolymerized with at least one monomer selected from the group consisting of tetrafluoroethylene and hexafluoropropene and Examples 5 through 10 speak to transport of ethylene oxide through films of such vinylidene fluoride copolymers, the invention is neither limited to articles for storage and transport of blood nor limited to fabrication of the article of the invention from films of the vinylidene fluoride copolymers. The article of the invention may be used to store and/or transport any biogenic fluid. The article of the invention may be fabricated as a film bag, a rigid or semirigid container having a single orifice, e.g. a cup, or a rigid or semirigid container having a plurality of orifices, e.g. a conduit, a "T"-shaped conduit connector, etc. Indeed, as used herein, the word "container" embraces bags, cups and conduits.

We claim the following:

1. An article for storing and transporting biogenic fluid comprising a container formed of additive-free uncharged transparent thermoplastic of a polymer of vinylidene fluoride copolymerized with at least one monomer selected from the group consisting of tetrafluoroethylene and hexafluoropropene, wherein said vinylidene fluoride constitutes at least sixty-two percent by weight of the copolymer composition, the permeability to ethylene oxide of said thermoplastic being at least approximately $1 \times 10^{-6}$ grams per minute of gaseous ethylene oxide per square centimeter of film of such thermoplastic having a thickness between 3 and 4 mils.

2. The article of claim 1 wherein said container is a bag formed from a film of said additive-free uncharged transparent thermoplastic.

3. The article of claim 2 wherein said film is at most about ten mils thick.

* * * * *